(12) United States Patent
Shaikh et al.

(10) Patent No.: US 9,150,907 B2
(45) Date of Patent: Oct. 6, 2015

(54) MICROFLUIDIC FLOW CELL ASSEMBLIES AND METHOD OF USE

(71) Applicant: GENERAL ELECTRIC COMPANY, Schenectady, NY (US)

(72) Inventors: Kashan Ali Shaikh, Clifton Park, NY (US); Mengli Wang, Niskayuna, NY (US); Adriana Ines Larriera Moreno, Albany, NY (US); Jessica Godin Karp, Niskayuna, NY (US); Christine Lynne Pitner, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/277,836

(22) Filed: May 15, 2014

(65) Prior Publication Data

US 2014/0248618 A1 Sep. 4, 2014

Related U.S. Application Data

(63) Continuation-in-part of application No. 13/458,092, filed on Apr. 27, 2012, now Pat. No. 8,900,529.

(51) Int. Cl.
*G01N 1/28* (2006.01)
*G01N 21/64* (2006.01)
(Continued)

(52) U.S. Cl.
CPC .............. *C12Q 1/6813* (2013.01); *B01L 3/5027* (2013.01); *B01L 3/502707* (2013.01); *G01N 33/54306* (2013.01); *B01L 9/527* (2013.01); *B01L 2200/027* (2013.01); *B01L 2200/0689* (2013.01); *B01L 2300/0816* (2013.01); *B01L 2300/0822* (2013.01); *B01L 2300/0867* (2013.01); *B01L 2300/0877* (2013.01); *B01L 2300/0887* (2013.01); *B01L 2300/123* (2013.01); *B01L 2400/0655* (2013.01);
(Continued)

(58) Field of Classification Search
CPC ................ B01L 2300/0816; B01L 2300/0887; B01L 3/5027; B01L 3/502738
USPC .................................................. 422/502–504
See application file for complete search history.

(56) References Cited

U.S. PATENT DOCUMENTS 5,147,606 A * 9/1992 Charlton et al. .............. 422/412
5,872,582 A   2/1999 Pan
(Continued)

FOREIGN PATENT DOCUMENTS

WO     2008031228 A1    3/2008

OTHER PUBLICATIONS

Yuen et al., "Low-Cost Rapid Prototyping of Flexible Microfluidic Devices Using a Desktop Digital Craft Cutter", Lab Chip, vol. 10, pp. 384-387, 2010.
(Continued)

*Primary Examiner* — Paul Hyun
(74) *Attorney, Agent, or Firm* — Eileen B. Gallagher

(57) ABSTRACT

A microfluidic flow cell subassembly, which may be assembled into a flow cell having fluidic connections outside of the main substrate, is described for encapsulating a sample to allow for subsequent controlled delivery of reagents to the sample, such as multiplexed in situ biomarker staining and analysis. The fluidic connectors are thin film fluidic connectors capable of connecting to a fluid delivery system. The subassembly may be sealed against a solid support to form a flow cell. Methods of use are also disclosed.

3 Claims, 12 Drawing Sheets

(51) Int. Cl.
*C12Q 1/68* (2006.01)
*G01N 33/543* (2006.01)
*B01L 3/00* (2006.01)
*B01L 9/00* (2006.01)
*B32B 37/00* (2006.01)
*B32B 37/18* (2006.01)
*B32B 38/00* (2006.01)

(52) U.S. Cl.
CPC .......... *B32B 37/0076* (2013.01); *B32B 37/182* (2013.01); *B32B 38/0008* (2013.01); *B32B 2535/00* (2013.01)

(56) References Cited

U.S. PATENT DOCUMENTS

| | | |
|---|---|---|
| 6,443,179 B1 | 9/2002 | Benavides et al. |
| 6,494,614 B1 | 12/2002 | Bennett et al. |
| 6,499,499 B2 | 12/2002 | Dantsker et al. |
| 6,503,359 B2 | 1/2003 | Virtanen |
| 6,509,085 B1 | 1/2003 | Kennedy |
| 6,729,352 B2 | 5/2004 | O'Connor et al. |
| 6,827,095 B2 | 12/2004 | O'Connor et al. |
| 7,028,536 B2 | 4/2006 | Karp et al. |
| 7,235,400 B2 | 6/2007 | Adey |
| 7,629,125 B2 | 12/2009 | Sood et al. |
| 7,657,070 B2 | 2/2010 | Lefebvre |
| 7,767,152 B2 | 8/2010 | Stead et al. |
| 7,927,865 B2 | 4/2011 | Meathrel et al. |
| 2001/0029983 A1 | 10/2001 | Unger et al. |
| 2008/0202694 A1 | 8/2008 | Serbicki et al. |
| 2009/0081464 A1 | 3/2009 | Summersgill et al. |
| 2009/0253163 A1 | 10/2009 | Xie et al. |
| 2009/0317896 A1 | 12/2009 | Yoo |
| 2011/0082049 A1 | 4/2011 | Endress et al. |
| 2011/0152121 A1 | 6/2011 | Park et al. |
| 2011/0312751 A1 | 12/2011 | Azimi et al. |
| 2012/0025521 A1 | 2/2012 | Baller et al. |
| 2012/0269701 A1 | 10/2012 | Linder et al. |
| 2013/0210148 A1 | 8/2013 | Gracias et al. |
| 2013/0287645 A1 | 10/2013 | Shaikh et al. |

OTHER PUBLICATIONS

Christensen et al., "Characterization of Interconnects used in PDMS Microfluidic Systems", Journal of Micromechanics and Microengineering, pp. 928-934, vol. 15, 2005.

Sabourin et al., "Interconnection Blocks with Minimal Dead Volumes Permitting Planar Interconnection to Thin Microfluidic Devices", Microfluidics and Nanofluidics, pp. 87-93, vol. 9, Issue 1, 2006.

Paruchuri, "Flexible Microfluidic Circuit with Embedded In-plane Valve", pp. 25-30, 2007.

Tsao et al., "Bonding of Thermoplastic Polymer Microfluidics", Microfluidics and Nanofluidics, pp. 1-16, vol. 6, Issue1, Jan. 2009.

Focke et al., "Lab-on-a-Foil: Microfluidics on Thin and Flexible Films", The Royal Society of Chemistry, vol. 10, pp. 1365-1386, 2010.

Cheek et al., "Chemiluminescence Detection for Hybridization Assays on the Flow-Thru Chip, a Three Dimensional Microchannel Biochip", Analytical Chemistry, Dec. 15, 2001.

Kim et al., "Characterization of DNA Hybridization Kinetics in a Microfluidic Flow Channel", Sensors and Actuators B: Chemical, vol. No. 113, Issue No. 1, pp. 281-289, Jan. 17, 2006.

Sieben et al., "Fish and chips: Chromosomal Analysis on Microfluidic Platforms", IET Nanobiotechnology, pp. 25-37, Jun. 2007.

Sieben et al., "An Integrated Microfluidic Chip for Chromosome Enumeration Using Fluorescence in Situ Hybridization", Lab on a Chip, 2008.

Chung et al., "Multiplex Preesure Measurement in Microsystems Using Volume Displacement of Particle Suspensions", Lab Chip, vol. No. 9 , 2009.

Kim et al., "Breast Cancer Diagnosis Using a Microfluidic Multiplexed Immunohistoch Emistry Platform", Plos One, May 2010.

Devadhasan et al., "Fish-on-a-Chip: A Sensitive Detection Microfluidic System for Alzheimer's Disease", Journal of Biomedical Science, May 28, 2011.

A copy of PCT Search Report and Written Opinion issued in connection with corresponding PCT Application No. PCT/US2015/027584 on Jul. 6, 2015.

A copy of PCT Search Report and Written Opinion issued in connection with corresponding PCT Application No. PCT/US2015/027549 on Jul. 13, 2015.

\* cited by examiner

*100*

+50μm

+30μm

+10μm

-10μm

-30μm

-50μm

DAPI

CEP17

Her2

MICROFLUIDIC FLOW CELL ASSEMBLIES AND METHOD OF USE

CROSS-REFERENCE TO RELATED APPLICATIONS

This application is a continuation-in-part to U.S. patent application Ser. No. 13/458,092 filed Apr. 27, 2012 and is related to U.S. patent application filed concurrently herewith under Ser. No. 14/277,503 the entire disclosures of both are incorporated herein by reference.

BACKGROUND OF THE INVENTION

The invention relates generally to the fabrication and use of a microfluidic flow cell subassembly for encapsulating a sample to allow for subsequent controlled delivery of reagents to the sample, such as multiplexed in situ biomarker staining and analysis of a mounted biological sample using dye cycling.

For multiplexed in situ biomarker analysis, tissue samples or tissue microarrays (TMA) mounted on glass slides need to be stained with multiple molecular probes to investigate biomarker expression or spatial distribution quantitatively or qualitatively. The staining and data collection processes are typically performed using time-consuming manual techniques that are susceptible to error. After staining, a coverslip must be placed over the sample in order to keep the sample wet during subsequent imaging (data collection). The coverslip must then be removed before the next round of staining. This process of cover slipping and de-cover slipping can result in loss of the sample or movement of the sample on the glass slide, which confounds downstream analysis. Staining is generally conducted by applying the staining reagent to the sample and letting it sit over the course of a pre-determined incubation. Thus, the staining time is dictated by molecular diffusion of the staining constituents from the bulk solution to the sample. Methods of actively mixing reagents on top of the sample during the incubation aim to ensure uniform staining across the sample and increase interaction between the staining constituents and the sample. However, such methods have a lower limit on reagent volume since they rely on inducing bulk fluid movement without areas of fluid separation that would affect staining uniformity.

Thus, a need exists for a system that can automate the in situ multiplexed biomarker analysis workflow while providing optimal conditions for reagent delivery and data collection. One way to control reagent delivery with small reagent volumes is to confine the reagents to an area close to the sample by using a fluidic channel. The diffusion length is determined by the height the channel, and fresh (well-mixed) reagents can be flowed through the channel to maintain the optimal reagent concentration near the sample.

In general microfluidic flow cells are comprised of one or more sealing layers sandwiched between two substantially flat substrate layers. The sealing layer creates the fluidic channel shape, forms one portion of the channel wall, and typically defines the channel thickness. This sealing layer can be formed by cutting or molding a defined shape out of a solid material, or by printing a liquid material that solidifies on one of the substrates. The two substrates enclose the fluidic channel and serve as the top and bottom channel walls. A leak-proof seal is made by clamping the sealing layer in between the substrates and/or adhering the layer to one or both of the substrates.

Furthermore, construction of the flow cell dictates that the fluidic interfaces, inlets and outlets, are formed in at least one of the substrate layers. This limits the choice of substrate materials since holes must be created through the entire substrate thickness without affecting the structural robustness. For instance, drilling holes in a glass coverslip is a time-consuming, costly process since care must be taken to avoid introducing weak points that may propagate cracks.

Thus, a microfluidic flow cell is needed that allows for a wide range of substrate materials and does not require fluidic connections to be made through any of the substrates.

BRIEF DESCRIPTION OF THE INVENTION

The present invention overcomes the aforementioned drawbacks by providing a microfluidic subassembly which may be assembled into a flow cell having fluidic connections outside of the main substrate.

According to one aspect of the present invention a microfluidic subassembly is disclosed having a stacked planar assembly. The stacked planar assembly comprises an adherent layer, a substrate layer, and a gasket layer where each layer is adhered to one another and the adherent layer and the gasket layer extend beyond the extents of the substrate layer. The planar assembly further comprises at least one thin film fluidic connector comprising at least one microfluidic channel in fluid connection with the stacked planar assembly which is positioned outside the boundaries of the substrate layer.

In accordance with yet another aspect of the invention, a microfluidic flow cell is disclosed comprising the subassembly described above and further comprising a solid support adhered to the microfluidic flow cell subassembly.

In accordance with another aspect of the invention a method is disclosed of analyzing a biological sample attached to a solid support using the of the microfluidic flow cell described.

Various other features and advantages of the present invention will be made apparent from the following detailed description and the drawings.

BRIEF DESCRIPTION OF THE DRAWINGS

The drawings illustrate an embodiment presently contemplated for carrying out the invention.

FIG. 9 is a schematic diagram of an assembled flow cell using alternative designs of the gasket and adherent layers.

FIG. 12 show images of magnetically-assisted fluidic connections that consist of small inner diameter tubing snugly fit and glued inside of a ring magnet; FIG. 12A shows a cylindrical magnet placed on the opposite side of the thin-film connector while

DETAILED DESCRIPTION OF THE INVENTION

Figure 1A:
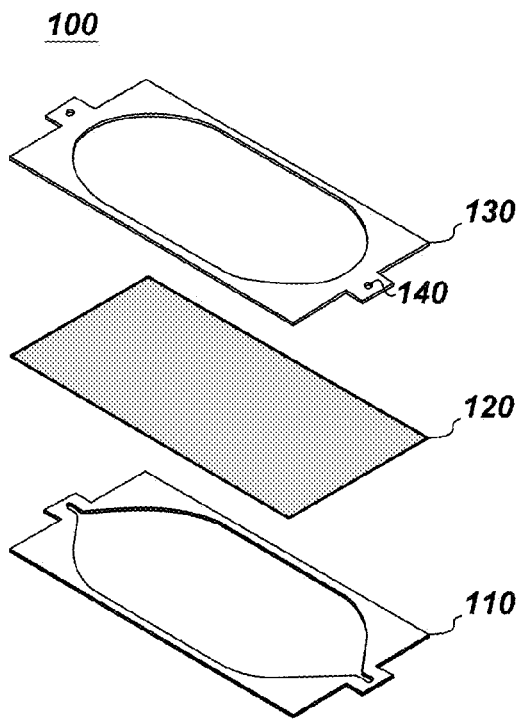
FIG. 1 is schematic diagram of a representative subassembly showing a stacked planner assembly; unassembled (A), viewed from the gasket side (B) and viewed from the adherent layer side (C).

To more clearly and concisely describe and point out the subject matter of the claimed invention, the following definitions are provide for specific terms, which are used in the following description and the appended claims.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques As used herein, the term "biological sample" refers to a sample obtained from a biological subject, including sample of biological tissue or fluid origin obtained in vivo or in vitro. Such samples may be, but are not limited to, a whole cell, tissues, fractions, and cells isolated from mammals including, humans, blood samples in whole or in part, as well as other biological fluids. The biological sample may be mounted or fixed onto a solid support, for example a tissue section, tissue microarray, or blood smear mounted on a microscope slide, or may be introduced into the flow cell after adhering the subassembly to the solid support.

As used herein, the term "consumable" refers to a disposable component that is designed for a single or limited use. In some situations the consumable may have a useful life that is less than that of the system with which it is used in, in other situations, the consumable may be a part, stored and manufactured separate from the system for which it is intended to be used.

In certain embodiments, the microfluidic subassembly provides a means of encapsulating a biological sample, so that it can sequentially be: stained with a dye, imaged with any high resolution microscope, the fluorescent reporter inactivated or quenched, then the cycle repeated. As used herein the microfluidic subassembly may also be referred to as a microfluidic chamber as it creates a chamber in the center of an assembled flow cell. As used herein the microfluidic subassembly may also be referred to as a subassembly. In certain embodiments, the subassembly is consumable such that the subassembly is designed for a single or limited use.

The subassembly device provides a means of encapsulating a sample within a chamber. In certain embodiments the sample is a biological sample mounted on a solid support such as a standard glass microscope slide allowing the sample to be maintained in a controlled environment during subsequent processing steps. The biological sample may be positioned on the solid support prior to encapsulation with the subassembly device which results in the formation of a flow cell. In certain embodiment, the biological sample may include, but is not limited to a whole cell, a tissue section, a tissue microarray, or a blood sample. In certain embodiments the tissue section may be a fixed tissue sample. In certain embodiments, the flow cell comprising the subassembly may be consumable such that the subassembly is permanently attached to the solid support for real time or near real time analysis. In certain embodiments, the flow cell as assembled may also serve to archive the sample for future testing or analysis.

The biological sample may also be attached to the solid support after flow cell formation by flowing it into the cell and trapping it via chemical or biological means, electrostatic interactions, non-specific adsorption, dielectrophoretic forces, magnetic force, optical tweezers, and physical entrapment by microstructures, or similar means. In certain embodiments, the flow cell containing the encapsulated sample may be archived intact for analysis at a later time.

In one embodiment the microfluidic flow cell formed using the subassembly does not need to be physically clamped to maintain a seal to the solid support or maintain the integrity of that seal.

In certain embodiments, the contents of the flow cell may be analyzed in-situ, using various optical, electrical, magnetic, or electromechanical devices in communication with the flow cell. In another embodiment, substances may be transported out of the flow cell for subsequent analysis. In one embodiment, the flow cell is used for multiplexed tissue staining and imaging as described in US patent application US2009253163A1, and U.S. Pat. No. 7,629,125. In still other embodiments the flow cell may be used for other cellular analysis technique or a combination of techniques involving morphology with or without extraction methods. Analysis techniques may include, but are not limited to, DNA analysis or amplification, RNA analysis or amplification, nucleic acid sequencing, protein analysis, antigen retrieval, Hematoxylin and Eosin staining (H&E), immunofluorescence staining (IF), immunohistochemical staining (IHC), fluorescent in-situ hybridization (FISH), or other histological and morphological staining techniques.

Figure 1B:
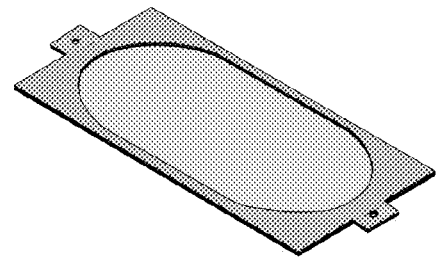
Figure 1C:
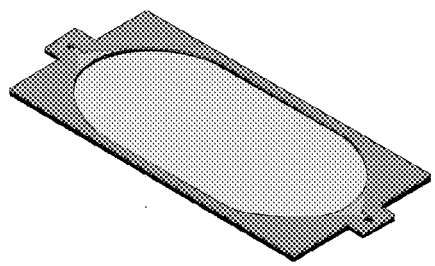

A representative embodiment of the subassembly is shown in FIGS. 1A and 1B and 1C. The subassembly device (100)

consists of a stacked planar assembly comprising an adherent layer (110) a substrate layer (120), and a gasket layer (130) where the gasket layer and the adhesive layer are extended beyond the substrate layer. The layers are adhered together and have holes positioned along the outer boundary of the adherent layer and gasket layer to form fluidic inlet/outlet ports (140). A fluidic inlet/outlet port may also be referred to herein as a port. FIG. 1B shows the subassembly viewed from the gasket (130) side and FIG. 1C shows the subassembly viewed from the adherent layer (110) side.

The substrate layer (120), in certain embodiments the substrate material may be comprised of glass, but may also be comprised of plastic, metal, silicon, ceramic, dielectrics, silicone or a combination thereof. In certain embodiments, the preferred material is glass or a substrate is a glass coverslip. In certain embodiments, such as when the substrate is a coverslip, the coverslip may be comprised of glass, such as silicate or borosilicate glass, or specialty plastics such as NUNC™ Brand Thermanox® coverslips made form polyolefins, that have the correct optical transparency. Fused quartz cover slips may also be used where ultraviolet transparency is required, e.g., for fluorescence microscopy.

Figure 2A:
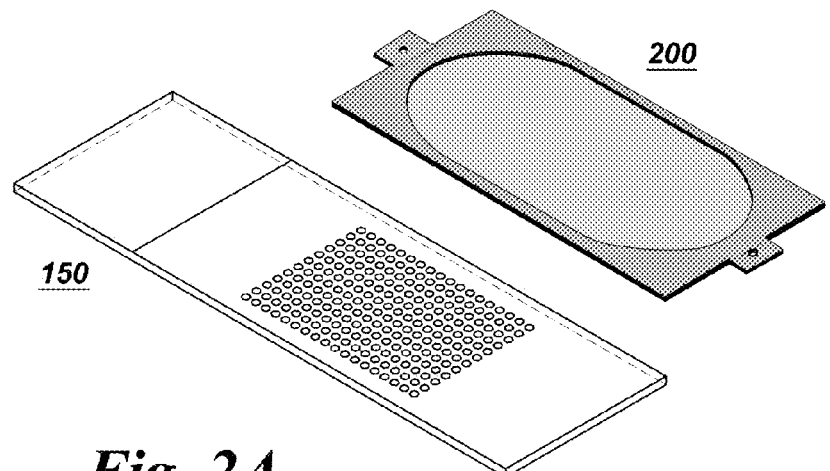
FIG. 2 is a schematic diagram of an assembled flow cell: (160) comprising the subassembly (100) adhered to a solid support (150); unassembled (A), viewed from the subassembly side (B) and viewed from the solid support side (C).
Figure 2B:
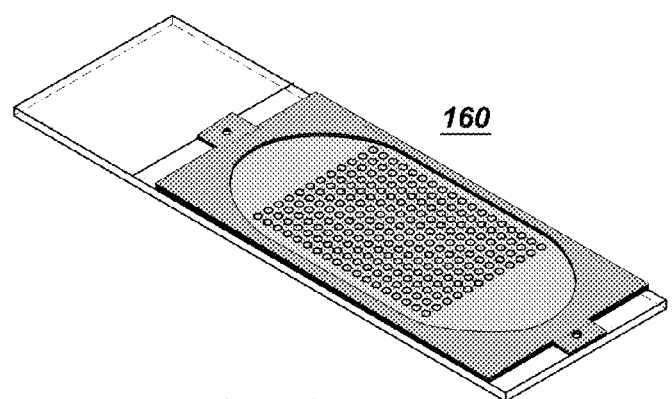
Figure 2C:
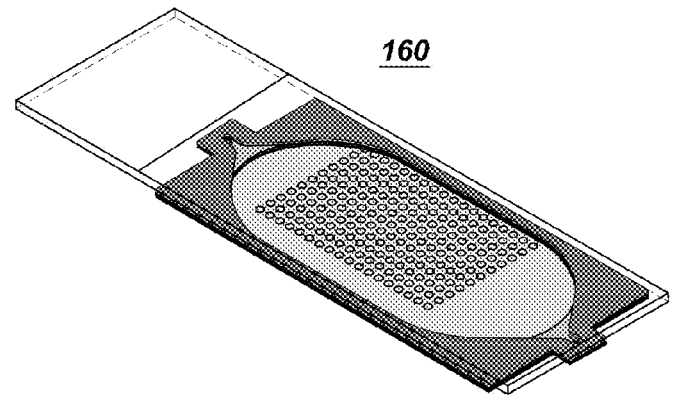

The subassembly (100) is capable of adhering to a solid support (150) as shown in FIG. 2. In the example of FIG. 2, a tissue microarray is mounted on the solid support. Adhering the subassembly effectively forms a microfluidic flow cell (160) sealed along its entire boundary. This is shown further in FIGS. 2B and 2C which shows the assembled flow cells from both sides, FIG. 2B is the flow cell depicted from the gasket side while 2C is depicted from the solid support side. In some embodiments, the total thickness of the subassembly may be designed to be about 25 to about 1200 µm, which is the combined thickness of the gasket between about 20 to about 1000 µm and the adherent layer between about 5 and about 200 µm.

In certain embodiments, one or both of the substrate (120) and the solid support (150) are optically transparent in a specified range of wavelengths. As such, optical analysis of materials/structures within the flow cell may be accomplished by either epi-illumination, or transmitted illumination if both are transparent. In the embodiment where the assembled flow cell may be used for multiplexed tissue staining and analysis, using both a transparent substrate and solid support allows for both epi-fluorescence imaging and transmitted brightfield imaging. This enables analysis of fluorescence-based molecular pathology as well as conventional brightfield imaging based on, for example, diaminobenzidine (DAB) staining or hematoxylin and eosin stain (H&E) chromogenic staining.

As used herein the term "adhered together" or "capable of adhering" refers to joining components or materials together to form a seal at the interface of the materials. Adhering may refer to the use of a chemical adhesive to form a bond, where the chemical adhesive includes but is not limited to silicones, epoxies, acrylics, room temperature vulcanizing materials (RTVs), thermoplastics, or a combination thereof. Adhering may also be accomplished by over molding one material over another to create a seal due to mechanical or chemical interactions at the interface of the two materials. In certain embodiments adhering may be accomplished through the application of external conditions such as pressure, temperature, or exposure to light or radiation. Adhering may result in a strong bond at the interface such that cohesive failure occurs at separation. In other cases, adhering may result in a bond at the interface which may be broken with a minimum amount of force such that the interface may be repositioned or the bond may be considered a temporary bond.

In certain embodiments, the solid support supports a fixed biological sample such that the sample is encapsulated by the resulting flow cell. The fluidic inlet/outlet ports (140) are configured to extend beyond the substrate (120) such that through-holes are not required in either the substrate (120) or the solid support (150).

In certain embodiments, the adherent material has an adhesive property and comprises a chemical adhesive such as, but not limited to, silicones, acrylics, epoxies, room temperature vulcanizing materials (RTVs), thermoplastics, or a combination thereof. In certain other embodiments, the adherent material may be an adhesive tape, silicone, thermoplastic elastomer, paraffin wax, printed adhesive material, or plastic film. In still other embodiments the adherent material may be an optical, thermal, chemical, or pressure sensitive adhesive where the application of light, heat or pressure enhances adherence. In still other embodiments, the adherent material is adhered to the substrate, solid support, gasket, or a combination thereof with the aid of plasma activation of the surfaces; for example air or oxygen.

Fluidic inlets and outlets ports are made by extending the adherent material beyond the edge of the substrate. In certain embodiments, the adherent material outside of the substrate may be capped by the gasket material. The gasket material may be composed of, but not limited to, silicone, thermoplastic elastomer, adhesive tape, rubber, or plastic. Fluidic inlets and outlets ports, leading into or out of the flow cell, may be comprised of through-holes present in the gasket material such that the ports are integral to the gasket structure. In still other embodiments, the port may be a different material than the gasket layer and is incorporated into the gasket to provide openings through the layer.

In certain embodiments, the fluidic inlets and outlet ports comprise thin film fluidic connectors which contain a microfluidic channel through which reagents can flow. The connector may be bonded directly to the microfludic flow cell through fluidic connection with the stacked planar assembly, and as such provides a low volume, easy-to-use fluidic connection between external macro-scale fluidics devices and the assembled flow cell, for example pumps, valves, and reservoirs.

In certain embodiments, in addition to a microfludic channel, the thin film may house microvalves to facilitate reagent switching, enable reagents storage wells to be directly integrated or coupled to the polymer thin film, and provide flow cell isolation during specific processing steps. Valves can isolate the flow cell to provide a leak-proof seal, to prevent liquid evaporation, or to hold a desired pressure or vacuum level. Valves can also facilitate filling the flow cell where a vacuum can be built up prior to opening the valves.

In certain embodiments, the thin film connectors may be comprised of a flexible plastic having generally a thickness of less than 1 mm. The flexible plastic may be, but not limited to, a polyimide film such as Kapton® (DuPont), cyclic olefin copolymer (COC), polyethylene terephthalate (PET), polymethyl methacrylate (PMMA), polycarbonate (PC), polytetrafluoroethylene (PTFE) such as Teflon® (DuPont), polystyrene (PS), polyethylene (PE), polysuflone (PSU), polyvinylchloride (PVC), polyetheretherketon (PEEK), polypropylene (PP), thermal- or pressure-sensitive adhesive, thermoplastic elastomer, or a silicone elastomer films. In certain embodiments, the plastic has sufficient chemical resistance to resist degradation by the reagents used.

In certain embodiments, the connectors are fabricated from multiple plastic layers which are laminated together to form the desired microfluidic features. In certain embodiments, one of more of the layers have pre-formed slots or grooves cut out or formed that, once the layers are laminated together, create an enclosed microfluidic channel. The layers can either be thermally bonded directly together, or may be bonded using adhesive interlayers including, but not limited to pressure-sensitive adhesives, B-stage adhesives, glues, chemical interlayers or a combination thereof. The chemical interlayer may be for example a chemical primer that is applied in a thin layer and may covalently attach to the surface.

Figure 3:
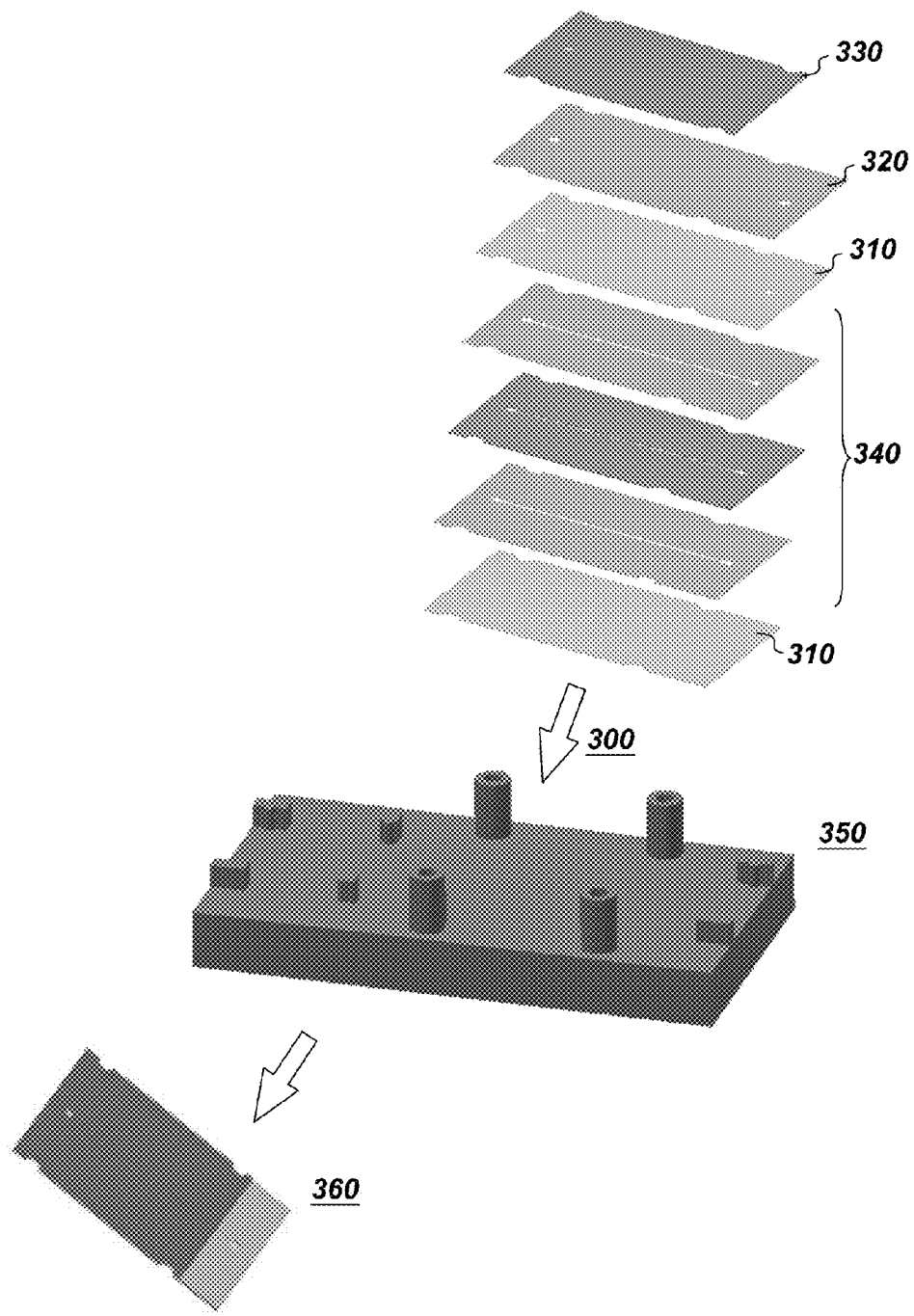
FIG. 3 is a schematic diagram of a connector assembly representing the laminate layers (300) which forms the thin film fluidic connector (360) with the assembly fixture (350).

FIG. 3 shows an assembly using one such laminate (300). As shown a channel laminate is formed through various layers of Kapton®, such as an upper and lower layer (310), pressure-sensitive adhesives (320), and a silicone gasket (330). A channel may be present in pre-formed layers (340). A fixture (350) may be used to align the individual layers during assembly to allow for reproducibility and tight tolerance in the alignment. This results in a fluidic channel enclosed within a polymer thin film connector (360), containing fluidic ports that allows fluidic communication with the channel.

Figure 4A:
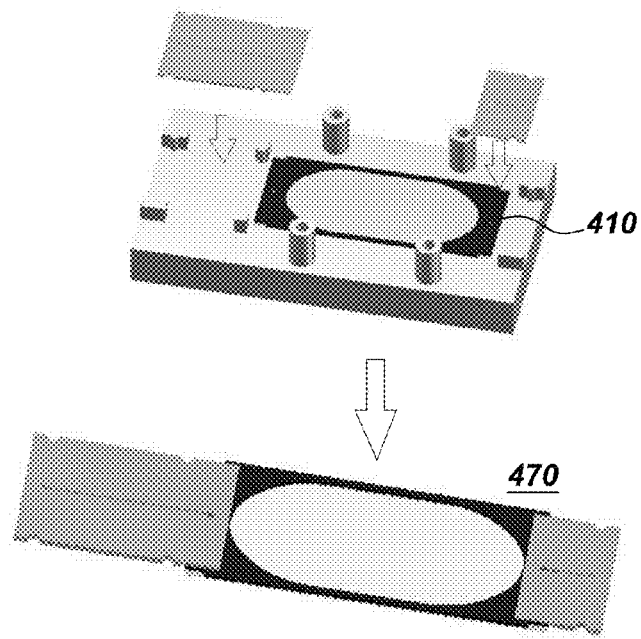
FIG. 4 is a schematic representing a thin film connector bonded first to the flow cell gasket material (410) as part of the subassembly (420) (FIG. 4A) which adheres to the solid support (430) (FIG. 4b) to form a microfluidic flow cell (440).
Figure 4B:
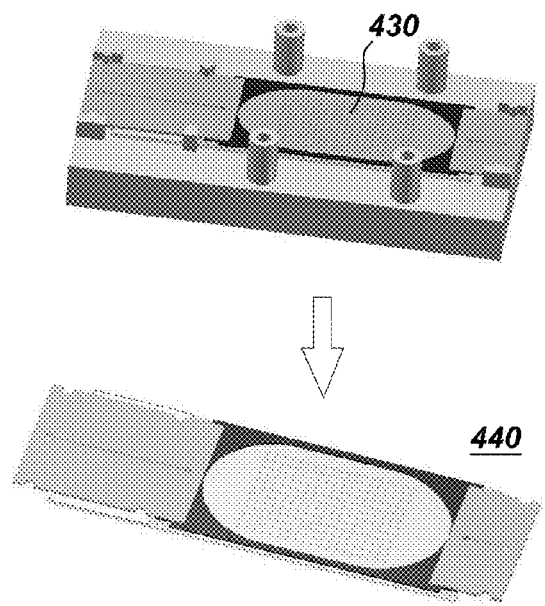

As shown in FIG. 4, in certain embodiments, the thin film connectors may be first bonded to the flow cell gasket material (410) (FIG. 4a) as part of the subassembly (420). The resulting subassembly may then be adhered to the biological sample (430) (FIG. 4b) to form a microfluidic flow cell (440). In certain other embodiments, the film connector may be part of the gasket material itself, where the gasket extends beyond the flow cell subassembly as a single piece constructor or where part of the gasket material forms as part of the laminate comprising the microfluidic channel.

In certain embodiments, the adhesive interlayers may optionally have microfluidic features cut through them. In certain embodiments, valves may be formed by a combination of silicone membranes and corresponding microfluidic channels and valves.

In certain embodiments, well-developed methods for building thin film electronics can be combined with methods for building microfluidic channels to realize integrated fluidics and electronics and enable heating/cooling, electromagnetic wave producing/transducing/sensing, pressure/vacuum producing/transducing/sensing, and flow/electrical sensing elements.

In certain embodiments, the thin film fluidic connector may be bonded directly to a silicone gasket layer of the consumable microfluidic flow cell. Alternatively, it may be bonded via pressure-sensitive adhesive to the edge of the flow cell coverslip, eliminating the need for the flow cell gasket layer.

In certain embodiments, alignment features in the thin film connectors enable simple registration in an instrument, such as when mounted on a microscope. The connectors allow for a de-coupling between the fluidic seal and the flow cell mounting, enhancing ease of use.

Figure 5:
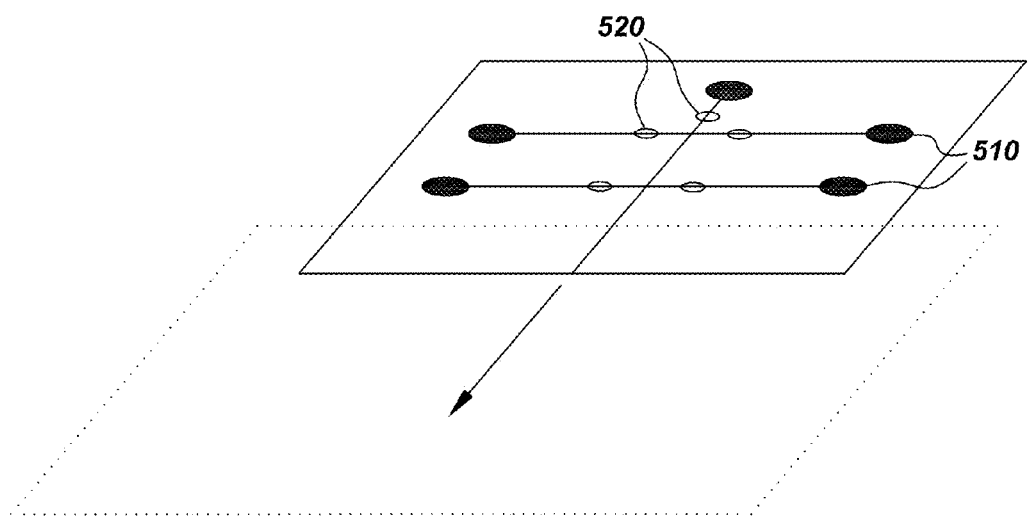
FIG. 5 is a schematic diagram showing a thin film connector configured with integrated reagent wells (510) and valves (520).

In certain embodiments, the thin film connectors are designed to allow for alternative fluidic connections. One port that serves as a single connection may be used, while other designs may allow for multiple inlet and outlet ports. In other embodiments, the port may interface with flow channels or valves used to direct or control flow. In still other embodiments, as shown in FIG. 5, the connector may be configured with integrated reagent wells (510) and valves (520) to provide for multiple inlets and flow of reagents into the flow cell with minimal reagent dilution.

In certain embodiments the valves may be incorporated directly into the thin film connectors or are in fluid connection with the connectors to control flow of reagents into and out of the flow cell.

In certain embodiments, electrical traces may be integrated in the polymer thin film, allowing for sensing and heating elements, as well as electronics to be closely coupled to the fluidic channels as described previously to enable heating/cooling, electromagnetic wave, producing/transducing/sensing, pressure/vacuum producing/transducing/sensing, and flow/electrical sensing elements. Thin film detectors, for example OLED, may also be integrated for optical sensing and detection.

Figure 6:
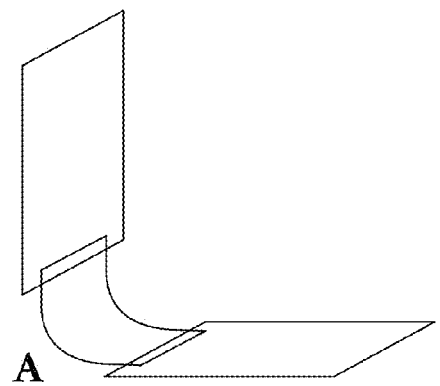
FIG. 6 is a schematic diagram showing fluidic modules arranged with thin film fluidic connections that are angled (A), twisted (B) or stacked to allow for multiple modules to be arranged in series (C).
Figure 6:
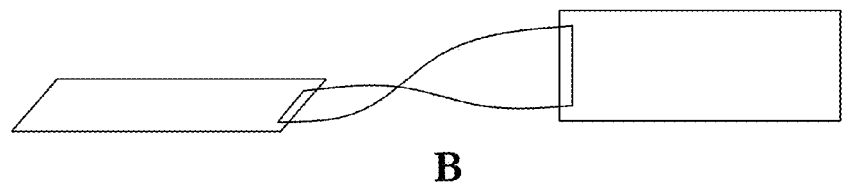
Figure 6:
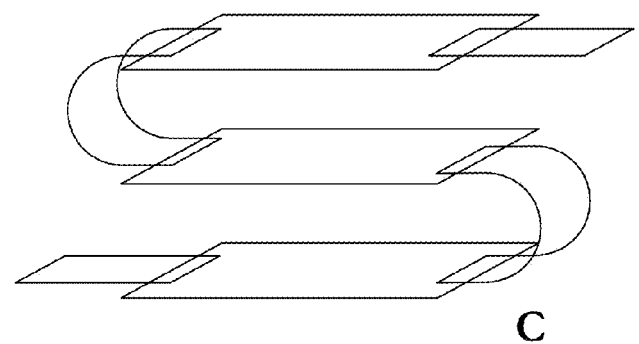

In certain embodiments, the thin film can be flexible, which allows for fluidic routing in three dimensions as well as allowing for gap filing where the distance between a connection or a position of a connection is not uniform or to allow switching or insertion between different apparatus of dissimilar sizes. This is shown in FIG. 6 which also allows for fluidic modules (e.g. flow cells) to be arranged with thin film fluidic connections that are angled (A), twisted (B) or stacked to allow for multiple modules to be arranged in series (C). This includes but is not limited to an 180° connection.

Figure 7A:
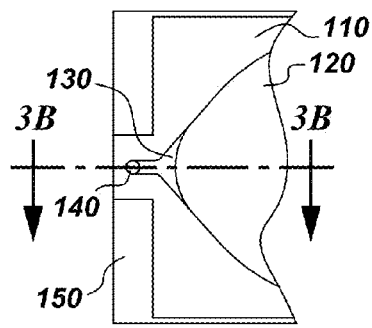
FIGS. 7A and 7B is a schematic diagram of two views showing the gasket layer may as a valve in the assembled flow.
Figure 7B:
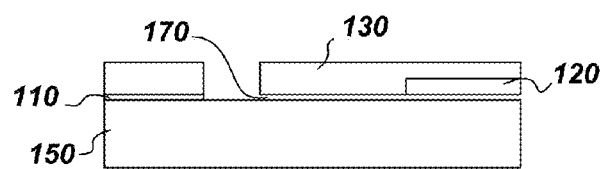
Figure 7C:
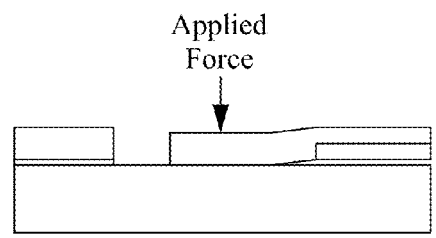
FIG. 7C is a schematic diagram representing how a fluidic valve is closed by deforming the gasket layer.

As shown in FIGS. 7A and 7B, in certain other embodiments, the gasket layer (130) may act as a valve to block the flow of reagents between the ports (140) and the assembled flow cell (160) and provide isolation of the contents within the flow cell. The valve is closed by deforming the gasket so that it contacts the solid support (150) in the channel area (170) between the substrate and the port (140) (FIG. 7C). This deformation can be induced by methods including, but not limited to, movement of a solid structure pushing against the gasket, and pneumatic pressure applied locally to a specified portion of the gasket. Other methods of deforming the gasket and sealing it against the solid support may also be used.

Figure 8A:
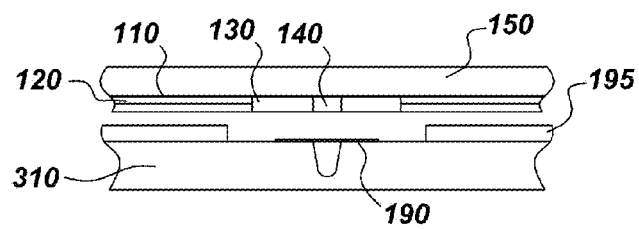
FIG. 8A is a schematic diagram of one embodiment where the fluidic connection fixtures comprises a raised ring or sealing device.
Figure 8B:
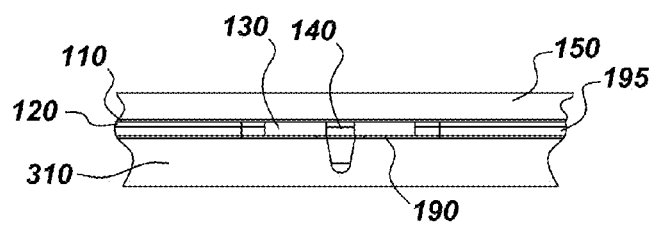
FIG. 8B is a schematic diagram showing how contacting the microfluidic flow cell against the raised sealing surface (190) forms a seal to the gasket layer.

FIG. 8A shows one embodiment where the fluidic connection may be accomplished where the fluidic connection fixture further comprises a raised ring or sealing device fixture (200). As shown contacting the microfluidic flow cell against the raised sealing surface (190) forms a seal to the gasket layer (FIG. 8B). A ledge (195) on the fixture may limit the gasket compression distance and provide a level surface on which to register the solid support to an external entity such as a microscope objective of an imaging device.

Figure 9A:
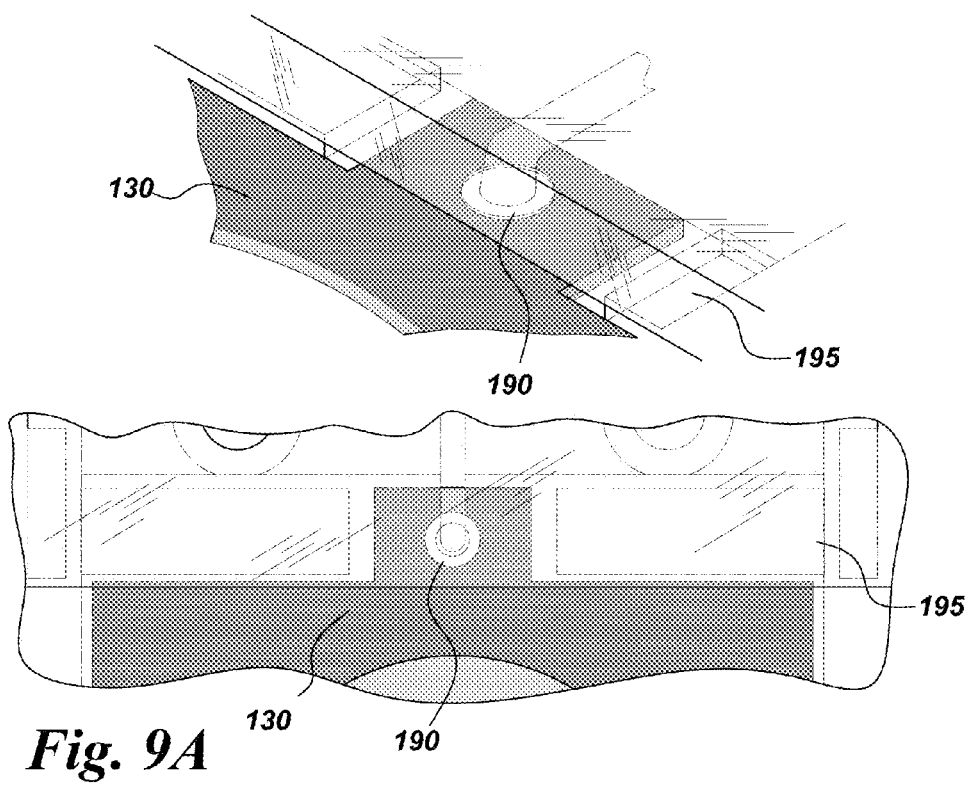
FIG. 9A is one representation of the raised sealing device showing the gasket (130) and the ledge (195).

FIG. 9A is one representation of the raised sealing device showing the gasket (130) and the ledge (195) in more detail. The gasket (130) is positioned against the raised surface.

In certain embodiments, the amount of compression is determined by the gasket thickness and the distance between the raises seal and the ledge. For example if the total thickness of the assembled flow cell is approximately 525 μm while distance between the seal and the ledge is approximately 500 μm, the compression distance is designed to be approximately 25 μm.

Figure 9B:
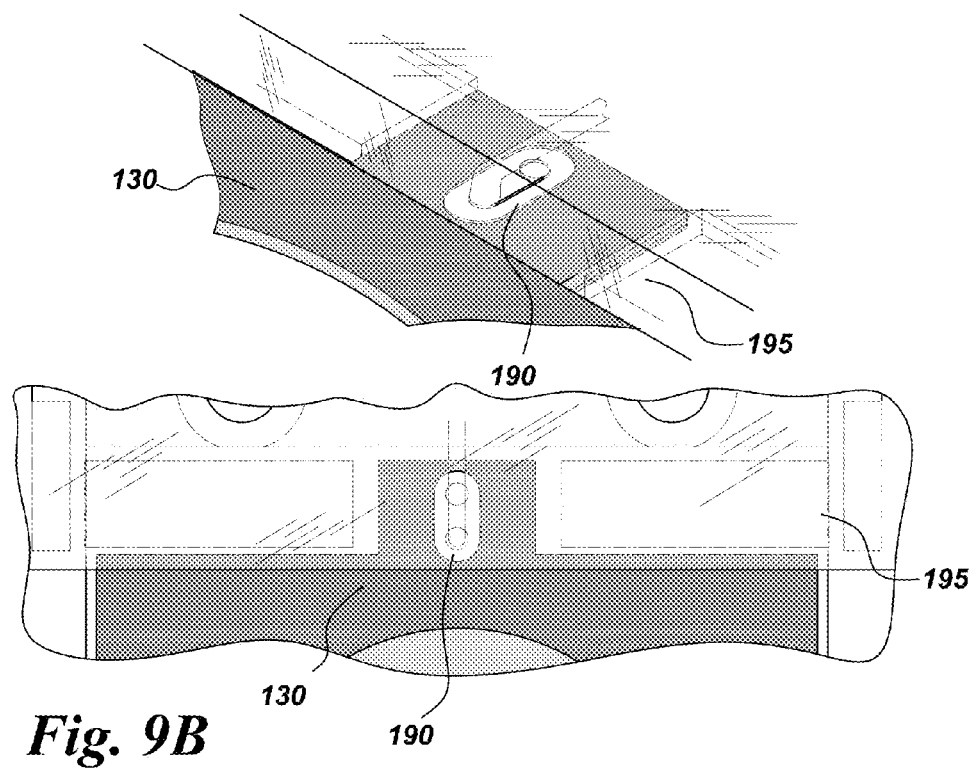
FIG. 9B shows where the flow channel may be formed with the gasket layer (130) as the bottom surface.

In another embodiment the compression tolerance may be reduced by forming a seal that completely surrounds the gasket area above the channel formed in the adherent layer (FIG. 9B), which prevents the gasket from deflecting towards the solid support. This is illustrated in FIG. 9B where the flow channel may be formed with the gasket layer (130) as the bottom surface. This allows for variable compression due to tolerances in manufacturing without adversely affecting the flow resistance of the connector.

In certain embodiments, the gasket is designed to be compressed by at least 5 μm and no more than 30 μm. In other embodiments, the compression distance is designed to be at least 5 μm but the maximum distance may be up to 200 μm if the compression does not deform the gasket. As represented to make a robust seal between the gasket and fluidic connector, it is desirable that the gasket be compressed by a distance greater than the surface roughness/variation of the gasket. In some embodiments, the gasket should not be compressed so much that it deforms and seals against the solid support surface (blocking off the channel extending beyond the substrate). The gasket compression should preferably be less than half the channel height. Assuming the gasket surface roughness is <1 μm after molding using a very smooth master mold, the thickness/surface variation is the dominant parameter. Variation in the gasket thickness may be on the order of ±5-10 μm, and a similar tolerance is expected of the step size of the fluidic connector. In certain embodiments, the target gasket may be defined as 25 μm±12.5 μm.

In certain embodiments, the solid support (150) may contain a biological sample. In certain embodiments, the bond strength of the subassembly (100) to the substrate (150) may be sufficient such that the assembled device (160) need not to be clamped to maintain a seal. The required bond strength may depend on the pressure drop generated under normal flow conditions, flexibility of the substrate and the solid support, normal operating temperature, and chemicals that come in contact with the subassembly materials and solid support.

The required height of the subassembly (100) and the related assembled flow cell (160) may be determined based on the thickness of the sample. Where the sample is a tissue section, it may have a thickness between about 1 μm to about 100 μm. In some embodiments, the tissue section may occupy up to a 25 mm by 50 mm area. This results in a small internal cell volume or holding capacity of the subassembly in the range of 1 μL to 1000 μL, preferably, 25 μL to 200 μL determined by the subassembly dimensions. The subassembly may be designed differently for different sample dimensions to minimize the internal cell volume while still enclosing the sample. In certain embodiments, the dimensional tolerance may be related to a compatible automated device or the control of reagent volume. For example in certain embodiments, the dimensional tolerance of the wall width or height may be ±10 μm. In other embodiments, the tolerance may be ±6.25 μm, in still other embodiments; the tolerance may be ±5 μm. The tolerance is such that it may further aid the use of the automated device.

If the subassembly (100) is mechanically flexible, it may bend when fluid flows through the assembled flow cell. The source of the mechanical flexibility may be from the adherent layer, gasket, the substrate, or a combination thereof. For example, in certain embodiments, the substrate (120) may be a non-rigid flexible polymer film or glass having sufficient flex modulus to deform without breakage. In other embodiments, the gasket may be over molded on to a glass cover slip, whereby the glass cover slip is the substrate layer (120).

As such, in certain embodiments, the gasket and the substrate are able to function as a flexible material layer. When flow is induced with positive pressure, the flexible material layer will bend away from the solid support and effectively create a larger chamber volume in the center of the flow cell. In these instances, the flow resistance will be smaller in the center and more of the flow will occur in the center. When flow is induced with negative pressure, the flexible material layer will bend towards the solid support and effectively create a smaller chamber volume in the center of the flow cell. This means that the outer edges of the flow cell will have the lower flow resistance and more of the flow will occur in these areas. As such the flexible material may function as a flow controller. In certain embodiments, the solid support (150) may be flexible and functional in a similar fashion.

In certain embodiments, this switchable flow resistance may be used to ensure uniform fluid delivery across the entire flow cell by flowing back and forth with sequential positive and negative pressures. Fluid would flow preferentially in the center area of the flow cell followed by preferential flow in the outer edges of the cell. This is especially useful for molecular pathology application where tissue staining is conducted with a very wide flow cell and where uniform staining is important.

The switchable flow resistance may also be used to ensure air bubbles do not enter the center of the flow cell. For example, when making a fluidic connection between the flow cell and fluidic delivery system, air can be introduced at the connection interface. By flowing with negative pressure after making such a connection, any air in the system will flow along the outer edges of the flow cell and then exit the cell. If the substrate was not flexible, the air may enter the center of the flow cell and may get trapped, depending on the cell dimensions and flow characteristics. These air bubbles may obstruct the fluid flow and prevent uniform fluid delivery to contents within the cell. Furthermore, using a mechanically flexible material, variation in flow resistance across the flow cell can be modulated to achieve more uniform fluid delivery as well as preferential flow to facilitate priming the system and preventing air entrapment in the cell.

In certain embodiments, the flexibility of the gasket and/or the substrate to function as a flexible material layer or lid also provides a method of providing for optimal high magnification imaging within the microfluidic flow cell. As such, in preferred embodiments the substrate is optically transparent for imaging in the appropriate wave length range such as, for example, where the substrate comprises a coverslip or coverslip material. As such, a flow chamber is obtained with a flexible, transparent lid; that can be pulled down against the sample, simulating a conventional coverslip solid support and improving image quality without damaging or removing the microfluidic chamber.

Figure 10:
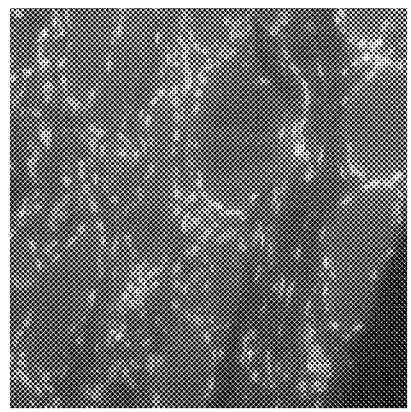
FIG. 10 shows results of imaging a human tissue section with a 20× magnification objective lens; the sequential images shows progression from a convex overfilled flow cell of 50 µm to a concave under filled flow cell of approximately −50 µm at various progressions.
Figure 10:
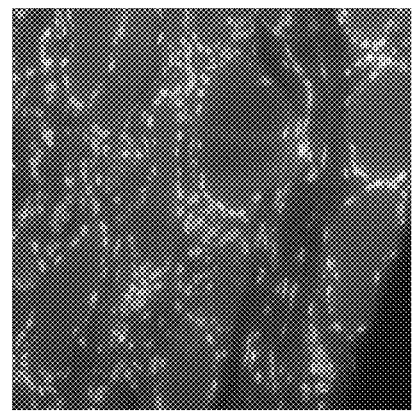
Figure 10:
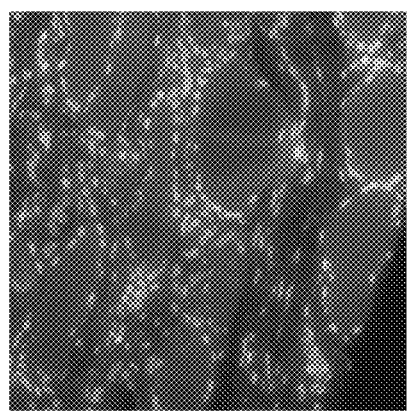
Figure 10:
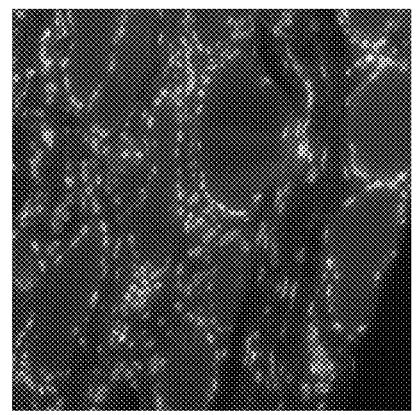
Figure 10:
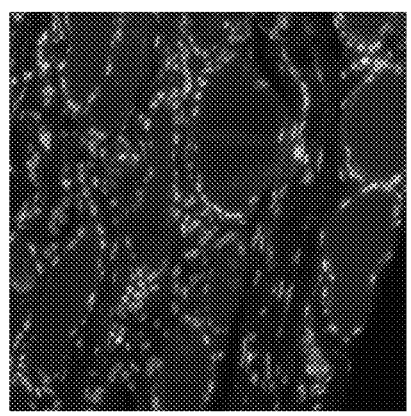
Figure 10:
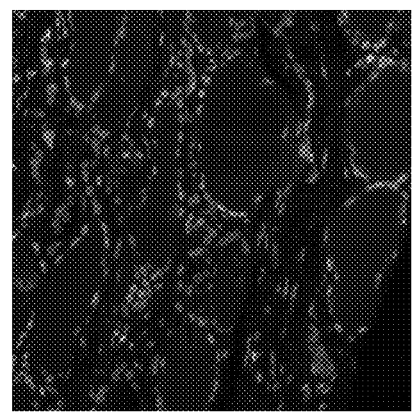

In certain embodiments the flexible material layer is configured to allow it to push away from, or bow towards, the sample as the chamber is pressurized, or depressurized. This is readily accomplished by adding or removing fluid from the flow cell chamber, gas or liquid, which is a typical operation in a microfluidic system. With a pump at the inlet and a pump at the outlet, the pumps can work in unison to flow liquids without significantly affecting the lid curvature. If bowing is desired, the pumps can be made to operate at mismatched speeds or even in opposite directions to achieve positive or negative curvature. With the chamber under negative pressure, the lid will pull down towards (or against) the sample, reducing the height of the fluid between the sample and the lid. This reduces the depth of fluid that the imaging system will image through, improving the image quality. In particular resolution/contrast when imaging through microfluidic channels may suffer due to light scattering and sub-optimal optical coupling through the fluid. As such the flexible lid creates a microfluidic chamber over the sample which, while allowing fluid flow as normal, further allows for the reduction of the total fluid height in the flow chamber during imaging FIG. 10 shows results of imaging a human tissue section with a 20× magnification objective lens. The sequential images shows progression from a convex overfilled flow cell of 50 μm to a concave under filled flow cell of approximately −50 μm at various progressions. Measurements are approximate z-height as measured by the microscope focus change. A zero point corresponds to an approximately flat flow cell glass surface. As shown, the quality of the image is changed based on the change of pressure in the chamber affecting the height of the liquid between the sample and the flexible lid.

In certain embodiments, the cover slips may be comprised of glass, such as silicate or borosilicate glass, or specialty plastics such as NUNC™ Brand Thermanox®, coverslips that have the correct optical transparency. Fused quartz cover slips may also be used where ultraviolet transparency is required, e.g., for fluorescence microscopy.

In certain embodiments, the deformation of the flexible lid is dependent on the volume capacity of the flow cell. In certain embodiments, the deflection of the lid may be related to the material used, for example if the material is silicone, significant flexibility can be achieved by the material acting as a flexible transparent bladder. In certain embodiments, the deflection of the lid may be plus or minus approximately 200 µm. In a preferred embodiment, the deflection is between −50 to +200 µm, and most preferred between −50 to +100 µm, and may result in a change of z-height from −20 to +50 µm. As such, the deformation of the flexible lid will allow for optimal imaging of the sample (maximum resolution and contrast) by minimizing the height of the fluid within the flow chamber, which minimizes spherical aberrations caused by the fluid.

In certain embodiments, the preferred deformation is almost no liquid between the sample and the flexible lid. Thus in one example, the deflection would be in the range of the thickness of the adherent layer minus the sample thickness (~20 um for a 25 um tall chamber with a 4 um tissue section).

In certain embodiments, the assembled flow cell (160) may be interfaced with a plastic cartridge that may house the fluids or dried reagents to be re-hydrated, that may flow into the chamber. In certain molecular pathology application, such a reagent cartridge may be used to house a specified panel of pre-packaged biomarkers for a particular test. The cartridge may also be designed to allow the addition of custom reagents by the user.

In certain embodiments the assembled flow cell comprises a subassembly and a solid support where the solid support is supporting a biological sample. The sample is fully encapsulated by the subassembly bonded to the solid support. In certain embodiments the adhering results in the subassembly being permanently or semi-permanently attached to the solid support whereby removal of the subassembly consumes the flow cell and may require assembly of a new flow cell for further analysis of the sample. The simple device structure enables low cost manufacturing such that the flow cell need not be reusable but may be a consumable component that remains affixed to a single solid support.

In certain embodiments the flow cell comprises at least one attachment point configured to match attachment points of another component of the device such as an imaging device stage, for example a microscope, a temperature control system or a fluidic device. In certain embodiments, the attachment points are configured to align the flow cell with the objective lens of an imaging device.

In certain embodiments, the resulting flow cell encapsulating the biological sample may be exposed to a variety of reagents and imaging processes. In certain embodiments, the flow cell containing the encapsulated sample may be archived intact for analysis at a later time or for post analysis after initial processing. In other embodiments the subassembly may adhere to a solid support supporting a material other than a biological sample. For example, the solid support may contain, but is not limited to, a chemical material, a mechanical structure, or combination thereof. In certain embodiments the material may be surface-bound chemicals, polymers, and mechanical structures such as, but not limited to micro-electromechanical sensors, actuators and flow obstruction elements. The resulting microfluidic flow cell may then be used in analysis or functioning of the contained materials.

In certain embodiments, the flow cell may be used in tissue or cellular analysis techniques including, but are not limited to, DNA analysis or amplification, RNA analysis or amplification, nucleic acid sequencing, protein analysis, antigen retrieval, Hematoxylin and Eosin staining (H&E), immunofluorescence staining (IF), immunohistochemical staining (IHC), fluorescent in-situ hybridization (FISH), or other histological and morphological staining techniques.

In certain embodiments, DNA fluorescence in-situ hybridization (FISH) or RNA FISH on tissue sections in a microfluidic chamber may be performed. As such in certain embodiments, an adherent flow cell is applied to a tissue slide to create a microfluidic chamber. FISH is then performed on the tissue by flowing in reagents, optionally sealing the flow cell (to prevent evaporation or allow for pressurization), and modulating the temperature of the flow cell as needed. After the process is complete, the chamber is optionally filled with mounting media and the tissue can be imaged in the flow cell. The flow cell remains on the tissue slide for subsequent processing steps or for storage.

Figure 11:
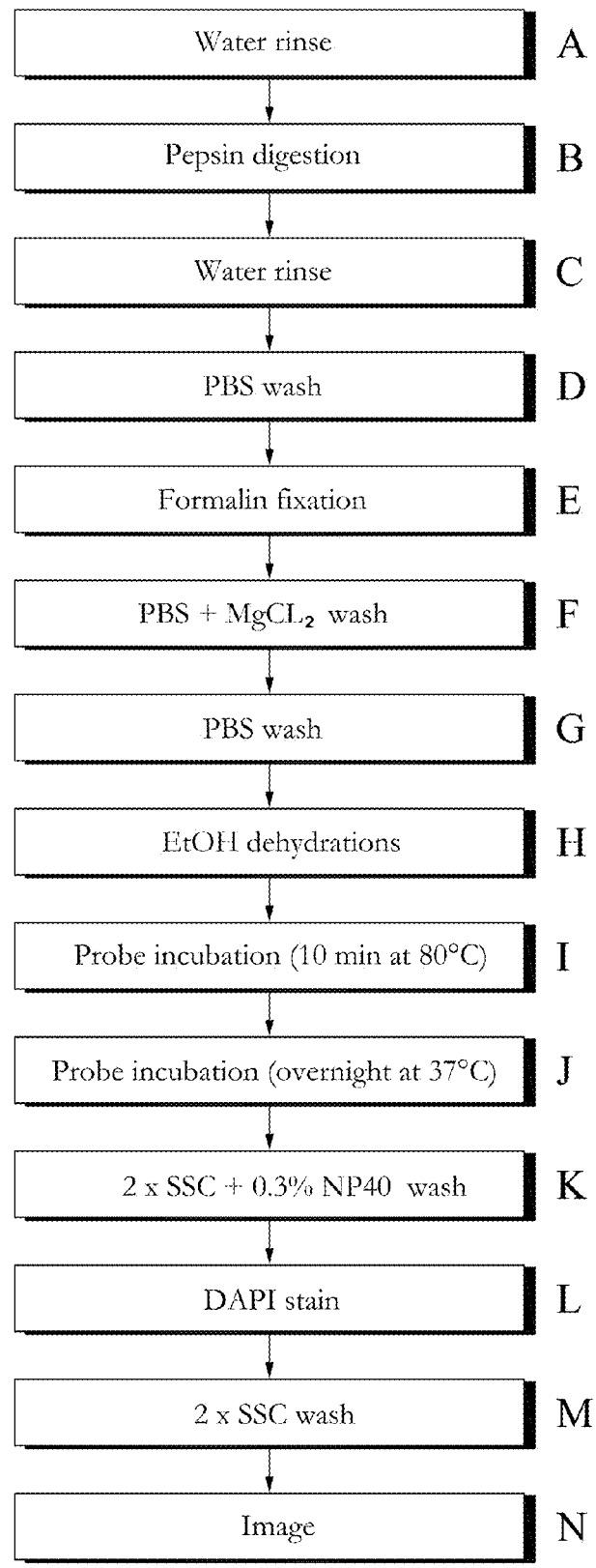
FIG. 11 is a process flow diagram representing one possible workflow for automating DNA FISH in the flow cell.

The flow cell creates a reliably airtight chamber in a consistent manner that is safe for the tissue. This approach also does not require subsequent removal of the chamber. The flow cell can be used to automate the fluidics to perform the FISH process, an example of which is shown in the process map of FIG. 11. The steps include, but are not limited to, water rinse (A), pepsin digestion (B), water rinse (C), PBS wash (D), formalin fixation (E), PBS+$MgCL_2$ wash (F), PBS wash (G), alcohol dehydration (H), incubation of the probe at varying conditions (I and J), subsequent washing with a solution of SSC and NP40 (K), DAPI staining (L), SSC wash (M) and imaging (N).

As such in other embodiments a general method of analyzing a biological sample attached to a solid support of the microfluidic flow may include (a) contacting the sample with reagents corresponding to techniques involving histological, morphological or molecular analysis by flowing the reagents through the fluidic connectors, (b) detecting a signal from biological sample, and (c) analyzing the histological, morphological, or molecular components of the sample. In other embodiments the signal from the sample may be deactivated and the process steps repeated.

EXPERIMENTAL

Experiments were conducted with tissue micro arrays encapsulated within a microfluidic flow cell and interfaced with a semi-automated thermo-fluidic system. The entire DNA FISH process was successfully implemented in the microfluidic flow cell and verified using this system.

A microfluidic flow cell confers the benefits of automation and repeatability to immunohistochemistry (IHC) processing and, therefore, the same benefits apply to DNA FISH. Compared to automation of IHC in a microfluidic flow cell, DNA FISH automation is more complex due to the addition of heat and wide variety of reagents.

The DNA FISH process included the sample preparation of baking slides for 1 hr. at 60° C., followed by slide clearing and hydration, and antigen retrieval, prior to assembling the flow cell. The DNA FISH protocol in the flow cell was optimized for Her2/CEP17 gene markers of the Vysis commercial probe distributed by Abbot Laboratories.

The flow cell protocol included a purging and priming step between each of the steps in order to minimize reagent dilution and avoid bubble entrapment. The purging and priming step consisted of applying suction from flow cell inlet until the tubing line was clear of liquid, manually using a $CO_2$ air gun to purge air from flow cell and push any liquid residue towards outlet, manually using a $CO_2$ air gun to purge air from outlet tubing, and priming the flow cell with the next reagent. Purging with $CO_2$ followed by rapid priming prevented bubble entrapment due to the higher solubility of $CO_2$ bubbles in water compared to air bubbles. Automation of the CO2 purge will be obvious to those skilled in the art.

The experimental setup consisted of the heating system along with syringe pumps for forward-direction fluid flow. Each reagent was flowed sequentially, at a specified flow rate and for a specified time, according to the protocol. The flow cell was then disconnected from the flow setup (discussed further below); the reagent syringe swapped out for the next reagent, and the tubing in the system was re-primed. The flow cell was emptied by first pulling liquid out (applying suction using a syringe), after which the flow cell was purged with $CO_2$ to push liquid out of the system and replace atmospheric air in the flow cell with $CO_2$ (more readily dissolves in water and helps to minimize trapped bubbles in the flow cell). While this approach was not automated, it was employed in order to minimize reagent dilution that would necessitate larger reagent volumes to completely replace one reagent with another inside the flow cell.

It is worth noting that that bubble formation may be observed in the cell as a result of water boiling under pressure. FISH probes are typically diluted in a specialized buffer, normally composed of a mixture of formamide, dextran, and saline-sodium citrate (SSC). Such a buffer has a higher boiling point than water, which should prevent boiling during DNA FISH incubation at 80° C. The flow cell design prevents evaporation of components of the solutions.

The flow cells utilized for DNA FISH demonstration are shown in FIG. 4. These flow cells incorporated thin-film fluidic connectors for easy connection to tubing for reagent flow. In this case, the connection to the pumping system was made by make-and-break magnetic connections between tubing and the thin film connectors. The connectors have an inlet, a thin microfluidic channel created by Kapton and adhesive layers, and an outlet that is bonded the flow cell. The inlet has a thin silicone layer to serve as a gasket. Magnets (~2,000-2,700 gauss) are placed on either side of the connectors in order to attract one another, clamping down on the connector and forming a tight seal with help from the gasket layer.

Figure 12A:
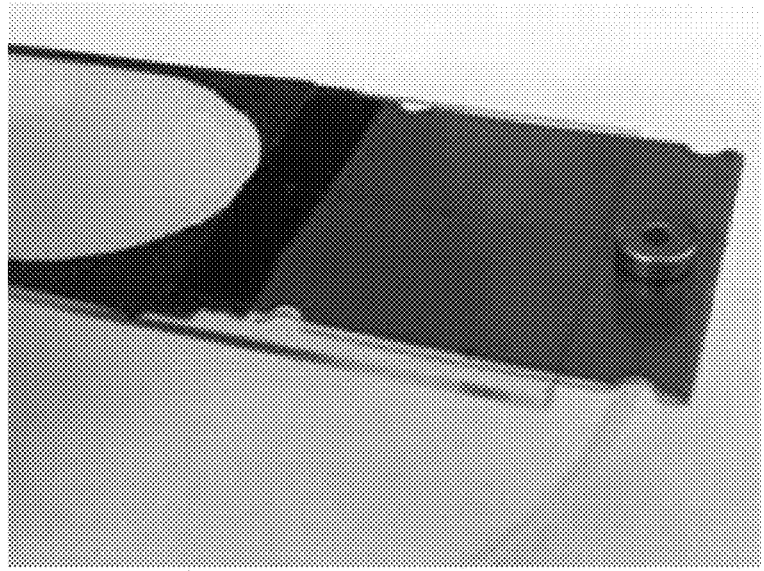
Figure 12B:
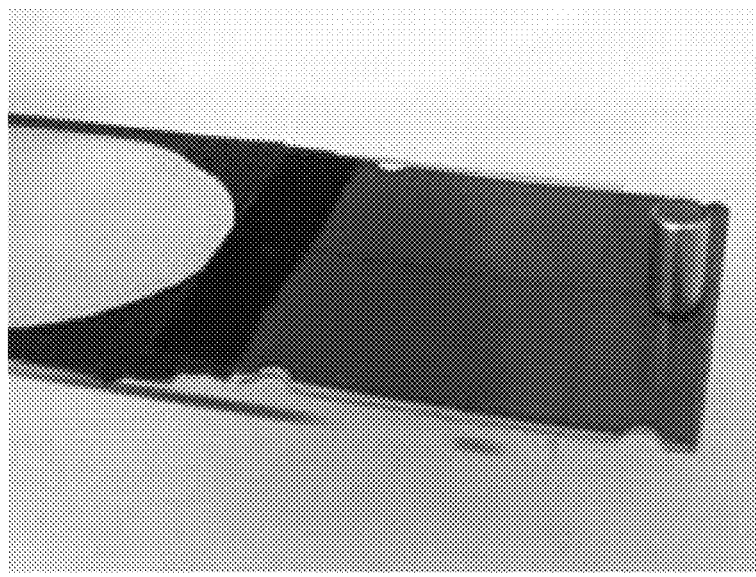
FIG. 12B shows how magnets are also used to block the ports and seal off the chamber.

Magnetically-assisted fluidic connections consist of small inner diameter tubing snugly fit and glued inside of a ring magnet. These connectors are placed against the inlet side of the thin-film connector, while a smaller cylindrical magnet is placed on the opposite side of the thin-film connector, as shown in FIG. 12A. The magnets attract, coupling the tubing to the thin-film connector and creating a tight seal between the two. Magnets are also used to seal off the chamber, as shown in FIG. 12b. In this case, small solid cylindrical magnets with a similar magnetic strength are used to create a tight seal against the inlet and outlet, preventing any fluid escape. This approach was used for the DNA FISH.

Figure 13:
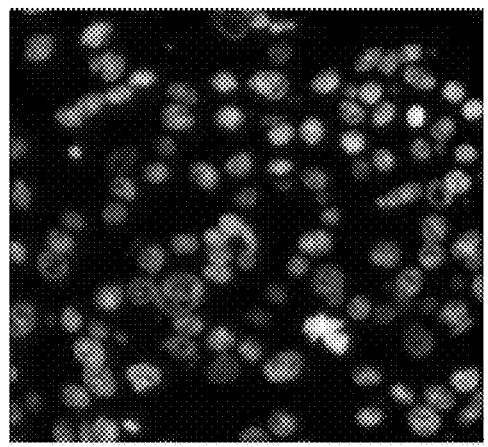
FIG. 13 are micrograph images of a successful DNA FISH experiment in the microfluidic flow cell showing DAPI, CEP17, and Her2 staining.
Figure 13:
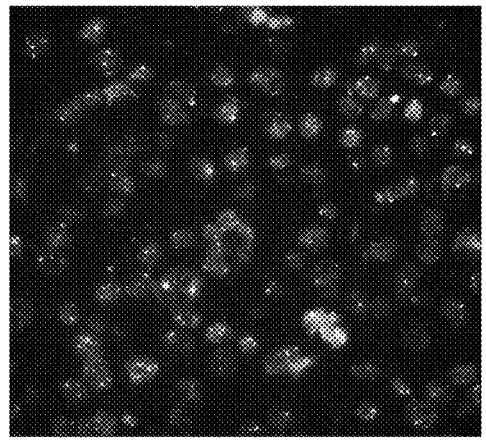
Figure 13:
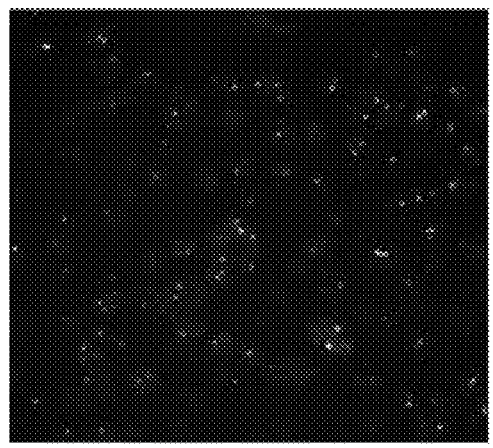

The images shown in FIG. 13, demonstrate a successful DNA FISH experiment in the microfluidic flow cell, beginning with digestion and ending with the application of mounting media followed by imaging.

As shown in FIG. 13, images include DAPI, CERP17, and Her2 staining. The nucleus appears appropriately digested, the FISH probes have hybridized correctly, and fluorescence signal was present for both CEP17 and Her2 channels.

The present invention has been described in terms of the preferred embodiment, and it is recognized that equivalents, alternatives, and modifications, aside from those expressly stated, are possible and within the scope of the appending claims.

What is claimed is:

1. A method of analyzing a biological sample attached to a solid support of a microfluidic flow cell where the microfluidic flow cell comprises:
    a microfluidic subassembly comprising:
    a stacked planar assembly comprising:
        an adherent layer;
        a substrate layer; and
        a gasket layer;
        where each layer is adhered to one another and the adherent layer and the gasket layer extend beyond the extents of the substrate layer; and
    at least one thin film fluidic connector where said connector comprises at least one microfluidic channel in fluid connection with the stacked planar assembly and is positioned outside the boundaries of the substrate layer; and
    the solid support adhered to the microfluidic subassembly;
    said method comprising:
    (a) contacting the sample with reagents by flowing the reagents through the at least one fluidic connector;
    (b) detecting a signal from the biological sample;
    (c) analyzing the signal;
    (d) optionally deactivating the signal and repeating steps a through c.

2. The method of claim 1 where the analysis of the biological sample comprises DNA analysis or amplification, RNA analysis or amplification, nucleic acid sequencing, protein analysis, antigen retrieval, Hematoxylin and Eosin staining (H&E), immunofluorescence staining (IF), immunohistochemical staining (IHC), fluorescent in-situ hybridization (FISH), or a combination thereof.

3. The method of claim 2 where the analysis comprises protein analysis, antigen retrieval, Hematoxylin and Eosin staining (H&E), immunofluorescence staining (IF), immunohistological staining (IHC), fluorescent in-situ-hybridization (FISH), or a combination thereof.

* * * * *